(12) United States Patent
Waldhoff et al.

(10) Patent No.: US 8,051,236 B2
(45) Date of Patent: Nov. 1, 2011

(54) PORTABLE AND MAGNETICALLY PROGRAMMABLE MEDICAL DEVICE SYSTEM

(75) Inventors: Gary J. Waldhoff, Maryland Heights, MO (US); Michael C. Dorsey, Edwardsville, IL (US)

(73) Assignee: Tyco Healthcare Group LP, Mansfield, MA (US)

( * ) Notice: Subject to any disclaimer, the term of this patent is extended or adjusted under 35 U.S.C. 154(b) by 0 days.

(21) Appl. No.: 12/894,731

(22) Filed: Sep. 30, 2010

(65) Prior Publication Data

US 2011/0022762 A1    Jan. 27, 2011

Related U.S. Application Data

(63) Continuation of application No. 12/372,395, filed on Feb. 17, 2009, now Pat. No. 7,873,772.

(51) Int. Cl.
*G06F 13/00* (2006.01)
(52) U.S. Cl. .......................................... 710/303; 439/38
(58) Field of Classification Search .......... 710/303–304; 601/6–7, 9–10; 439/38–40; 340/10.42; 604/319, 604/317–318, 322–326
See application file for complete search history.

(56) References Cited

U.S. PATENT DOCUMENTS

| | | |
|---|---|---|
| 4,569,674 A | 2/1986 | Phillips et al. |
| 4,650,476 A | 3/1987 | Telang |
| 4,661,093 A | 4/1987 | Beck et al. |
| 4,710,165 A | 12/1987 | McNeil et al. |
| 4,747,843 A | 5/1988 | Felix et al. |
| 6,071,267 A | 6/2000 | Zamierowski |
| 6,142,982 A | 11/2000 | Hunt et al. |
| 6,685,681 B2 | 2/2004 | Lockwood et al. |
| 6,752,794 B2 | 6/2004 | Lockwood et al. |
| 6,755,807 B2 | 6/2004 | Risk, Jr. et al. |
| 6,764,462 B2 | 7/2004 | Risk, Jr. et al. |
| 6,856,821 B2 | 2/2005 | Johnson |
| 6,951,553 B2 | 10/2005 | Bubb et al. |
| 7,004,915 B2 | 2/2006 | Boynton et al. |
| 7,022,113 B2 | 4/2006 | Lockwood et al. |
| 7,128,735 B2 | 10/2006 | Weston |
| 7,195,624 B2 | 3/2007 | Lockwood et al. |
| 7,216,651 B2 | 5/2007 | Argenta et al. |
| 7,316,648 B2 | 1/2008 | Kelly et al. |
| 7,338,482 B2 | 3/2008 | Lockwood et al. |
| 7,523,741 B2 | 4/2009 | Kochanowski et al. |
| 7,758,555 B2 | 7/2010 | Kelch et al. |
| 7,846,141 B2 | 12/2010 | Weston |
| 7,871,390 B2 | 1/2011 | Rambod et al. |
| 7,873,772 B2 | 1/2011 | Waldhoff et al. |
| 2005/0038674 A1 | 2/2005 | Braig et al. |
| 2005/0203469 A1 | 9/2005 | Bobroff et al. |
| 2005/0222544 A1 | 10/2005 | Weston |
| 2005/0261642 A1 | 11/2005 | Weston |
| 2007/0225663 A1 | 9/2007 | Watt et al. |
| 2008/0071235 A1 | 3/2008 | Locke et al. |
| 2010/0081473 A1 | 4/2010 | Chatterjee et al. |
| 2010/0087071 A1 | 4/2010 | DiFonzo et al. |

OTHER PUBLICATIONS

Office action issued Jun. 23, 2010 in related U.S. Appl. No. 12/372,395; 10 pgs. Response filed Aug. 13, 2010 to Office Action dated Jun. 23, 2010 from related U.S. Appl. No. 12/372,395; 7 pgs.

*Primary Examiner* — Clifford Knoll
(74) *Attorney, Agent, or Firm* — Elias Domingo

(57) ABSTRACT

A medical device system includes a portable medical device and a docking unit on which the medical device can be removably mounted. The docking unit is configured to communicate with a controller of the medical device when the medical device is mounted on the docking unit to instruct the controller to execute a selected program.

13 Claims, 7 Drawing Sheets

US 8,051,236 B2

PORTABLE AND MAGNETICALLY PROGRAMMABLE MEDICAL DEVICE SYSTEM

CROSS-REFERENCE TO RELATED APPLICATIONS

This application is a continuation application of U.S. Ser. No. 12/372,395, filed Feb. 17, 2009, the entirety of which is incorporated herein by reference.

FIELD OF THE INVENTION

The present invention generally relates to a portable and programmable medical device system.

BACKGROUND OF THE INVENTION

Portable, programmable medical devices are becoming more common and beneficial for treating patients. Some of these medical devices may be so small and lightweight that the patient is not confined to bed. In that case, the portable, programmable medical device gives the patient freedom to do some, if not all, of his/her normal day-to-day activities as he/she receives treatment. Other of these medical devices are readily moved about (i.e., portable), but still restrict the patient's freedom of movement. The device may include a controller that is programmed for controlling an operation of the device. With some portable and programmable medical devices, it is desirable to restrict the patient or other non-authorized person from deselecting the selected program or selecting another program during use.

SUMMARY OF THE INVENTION

In one aspect, a medical device system generally comprises a portable medical device including a controller programmed to selectively execute at least two programs for controlling at least one operation of the medical device. A docking unit on which the medical device can be removably mounted comprises an operator interface for selecting a program from said at least two programs. The docking unit is configured to communicate with the controller of the medical device when the medical device is mounted on the docking unit to instruct the controller to execute the selected program. The controller of the medical device is configured to control the medical device according to the selected program when the medical device is removed from the docking unit. The docking unit includes at least one magnet disposed in the docking unit for generating a magnetic field. The medical device includes at least one magnet sensor for detecting the magnetic field. The magnet is movable in the docking unit.

In another aspect, a docking unit on which a portable medical device can be removably mounted, where the medical device includes a magnet sensor and a controller programmed to selectively execute at least two programs for controlling operation of the medical device generally comprises an operator interface for selecting a program from said at least two programs. At least one magnet for generating a magnetic field is movable in the docking unit. The docking unit is configured to communicate with the controller of the medical device when the medical device is mounted on the docking unit to instruct the controller to execute the selected program.

Other objects and features will be in part apparent and in part pointed out hereinafter.

BRIEF DESCRIPTION OF THE DRAWINGS

Corresponding reference characters indicate corresponding parts throughout the drawings.

DETAILED DESCRIPTION OF THE DRAWINGS

Figure 1:
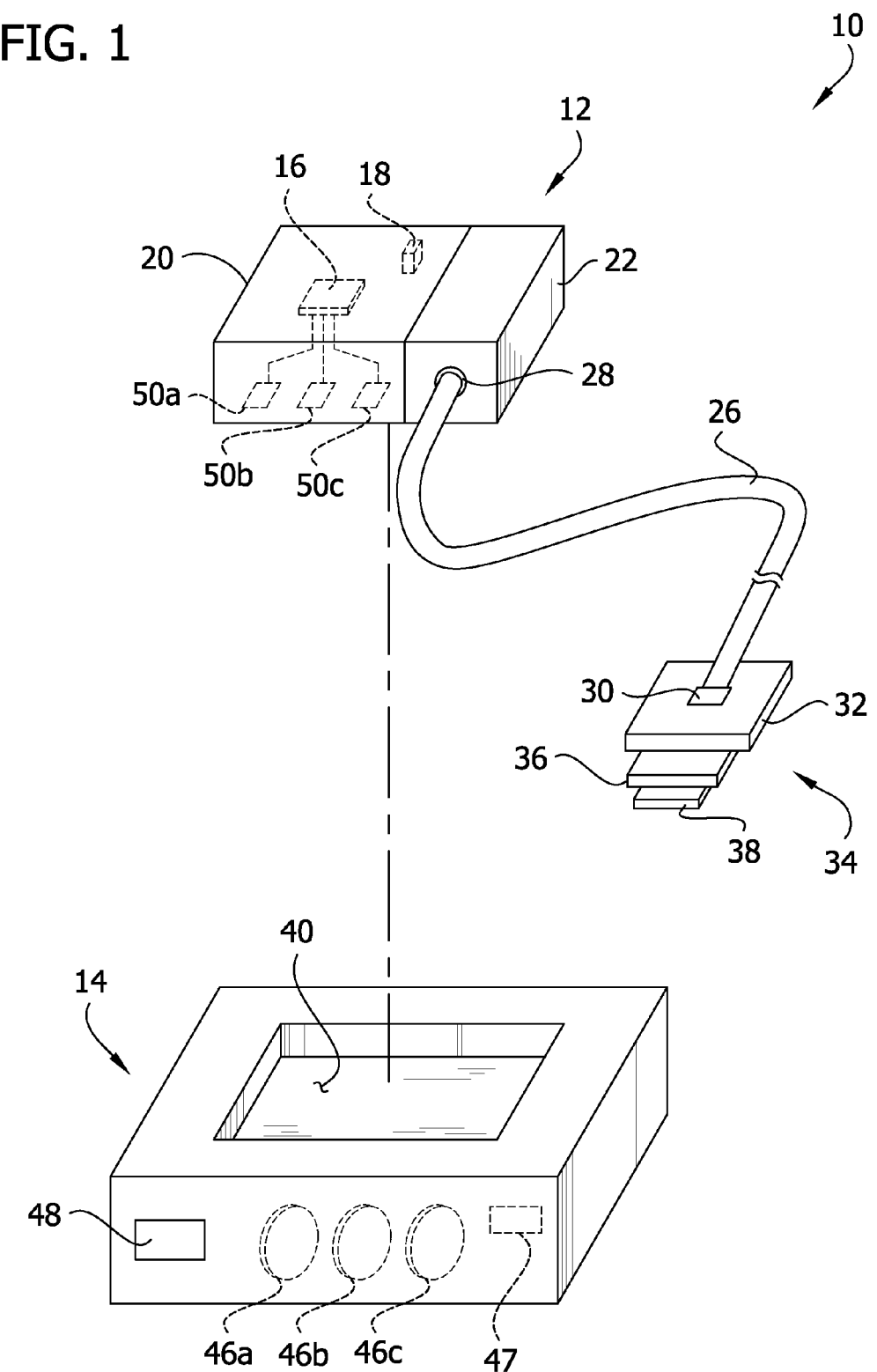
FIG. 1 is a schematic of a first embodiment of a negative pressure wound therapy system illustrating a negative pressure unit removed from a docking unit.

Referring to the drawings, FIGS. 1-7 illustrate several embodiments of a portable and programmable medical device constructed according to the teachings of the present disclosure. As will be explained in detail below, in general, each embodiment of the portable medical device system comprises a portable medical device and a docking unit. The portable medical device includes a controller for controlling an operation of the device, and the docking unit is configured to communicate to the controller to allow a user to select a program for execution by the controller for controlling an operation of the device when the device is removed from the docking unit.

Figure 2:
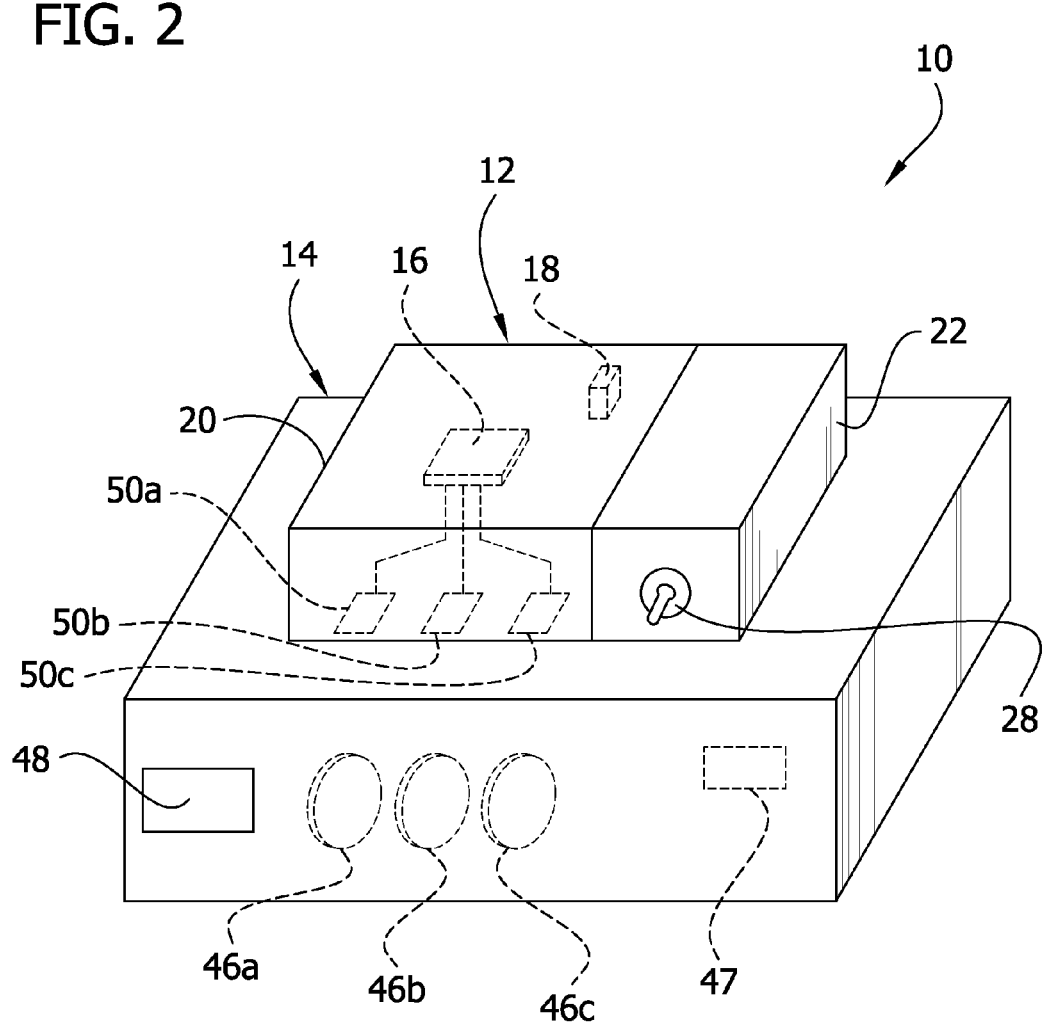
FIG. 2 is a schematic of the negative pressure wound therapy system illustrating the negative pressure unit mounted on the docking unit.
Figure 3:
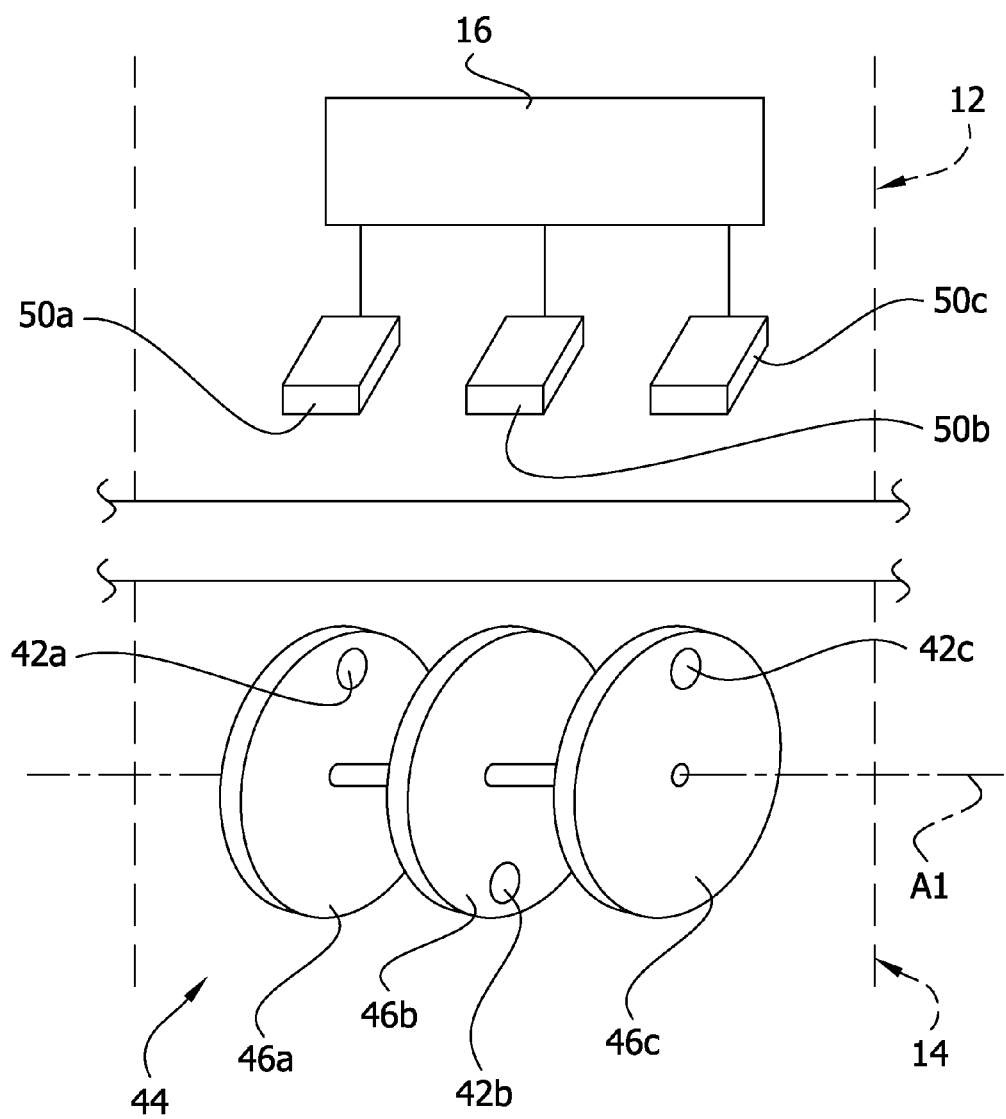
FIG. 3 is an enlarged, partial schematic of the negative pressure wound therapy system illustrating interactions between proximity actuators and proximity detectors.

Referring first to FIGS. 1-3, a first embodiment of a portable medical device is a negative pressure wound therapy system, generally indicated at 10. The negative pressure wound therapy system comprises a negative pressure unit, generally indicated at 12, and a docking unit, generally indicated at 14, which communicates with a controller 16 in the negative pressure unit. More specifically, the docking unit 14 instructs the controller 16 to execute a pump-operating program for controlling operation of the negative pressure unit in a predetermined manner. It is understood that the docking unit 14 may instruct the controller 16 to execute a program other than one that operates the pump. For example and without limiting the generality of the foregoing, other programs may change or select one or more of the following: beeper volume, display setting (backlight, contrast, ward name, language, etc.), anti-theft settings, settings lock, external communication settings, various diagnostic test (probe, LCD, battery, voltage, etc.). In the illustrated embodiment, the docking unit 14 communicates wirelessly with the controller 16 in that the docking unit does not send instructions over electrical wires or electrical contacts. It is understood that the docking unit 14 may communicate with the negative pressure unit controller 16 over electrical wires or electrical contacts without departing from the scope of the present invention.

The controller 16 and a vacuum pump 18 are contained within a housing 20 of the negative pressure unit 12. A canister 22 is removably secured to the housing 20 and is fluidly connected to the vacuum pump 18. Fluid tubing 26 is fluidly connected at one of its ends to the canister 22 via a canister inlet port 28. The fluid tubing 26 is fluidly connected at its opposite end to a dressing inlet port 30 secured to a flexible seal 32 of a wound dressing construction, generally indicated at 34. The wound dressing assembly also includes a gauze or foam layer 36 and a non-adherent wound contact layer 38, although it may include other components without departing from the scope of the present invention. As is generally known in the art, the wound dressing construction 34 is applied to a wound on a patient so that dressing inlet port 30 is in sealed fluid communication with the wound bed. The vacuum pump 18 is in fluid communication with the wound bed via the canister 22 and the fluid tubing 26. As a result, the vacuum pump 18 is able to create a negative pressure at the wound bed, and fluids and other exudates at the wound bed are drawn into the fluid tubing 26 and captured in the canister 22. The negative pressure unit 12 may include a hydrophobic filter (not shown) in the canister 22 or the housing 20 to prevent exudates from entering the vacuum pump 18. Other mechanisms for preventing exudates from entering the vacuum pump do not depart from the scope of the present invention. The negative pressure unit 12 may include other components and features without departing from the scope of the present invention.

As discussed above, the docking unit 14 communicates with the negative pressure unit controller 16 to instruct the controller to execute a pump-operating program, which may be one of a plurality of different programs. In one example, one pump-operating program may include instructions to apply continuous suction at the wound site at a selected pressure; another, different pump-operating program may include instruction to apply intermittent suction at the wound site at selected time intervals. Other pump-operating programs include instructions to apply continuous suction at the wound site with varying selected pressure level intervals and instructions to apply intermittent suction at the wound site with varying selected pressure levels and time intervals. Other pump-operating programs do not depart from the scope of the present invention.

In a first illustrated embodiment, the docking unit 14 includes a recess 40 for receiving the negative pressure unit 12 and mounting it on the docking unit. Other ways of mounting the negative pressure unit 12 on the docking unit 14 do not depart from the scope of the present invention. First, second and third permanent magnets 42a, 42b, 42c, respectively, inside the docking unit are located proximate to the recess 40. The permanent magnets 42a, 42b, 42c are mounted on an actuator mechanism 44. In the illustrated embodiment, the actuator mechanism 44 includes generally aligned first, second and third disks 46a, 46b, 46c that are independently rotatable about a common axis A1. Each magnet 42a, 42b, 42c is mounted on a corresponding one of the disks 46a, 46b, 46c, generally adjacent to a periphery of the disk. The disks are independently rotatable in the docking unit 14, so that each magnet 42a, 42b, 42c is independently moveable between a detection position and a non-detection position, as explained in more detail below. In the illustrated embodiment, a controller 47 in the docking unit 14 controls the actuator mechanism 44 and the movement of the disks 46a, 46b, 46c. A user interface 48 on the docking unit 14 allows a user to input instructions to the controller 47 to control movement of the magnets 42a, 42b, 42c. As explained below, the user interface 48 may include a plurality of buttons (not shown), each of which pertains to one of the pump-operating programs of the negative pressure unit 12. Other ways of moving the disks 46a, 46b, 46c do not depart from the scope of the present invention. Moreover, actuator mechanisms other than rotating disks can be used. For example, slide bars may be used in lieu of rotating disks. Other actuator mechanisms do not depart from the scope of the present invention.

Each magnet 42a, 42b, 42c is capable of activating a corresponding one of first, second and third proximity sensors 50a, 50b, 50c located in the negative pressure unit 12. By way of example but not limitation, these sensors may be Hall-effect sensors. When the negative pressure unit 12 is mounted on the docking unit 14, each magnet 42a, 42b, 42 is positioned in either the above-stated detection position (e.g., magnets 42a, 42c in FIG. 3), in which a displacement between the magnet and the corresponding Hall-effect sensor 50a, 50b, 50c is within a range in which the sensor senses or detects the magnetic field of the magnet, or the above-stated non-detection position (e.g., magnet 42b in FIG. 3), in which a displacement between the magnet and the corresponding Hall-effect sensor is outside the range in which the sensor senses or detects the magnetic field of the magnet. Each Hall-effect sensor 50a, 50b, 50c sends a first signal to the controller 16 when the sensor senses (e.g., is activated by) the corresponding magnet 42a, 42b, 42c and sends a second signal or no signal to the controller when the sensor does not sense (e.g., is not activated by) the corresponding magnet.

The sensors 50a, 50b, 50c send a combination of signals to the controller 16. The characteristic of the combination of signals is dependent on the position of each of the magnets 42a, 42b, 42c with respect to the corresponding sensor 50a, 50b, 50c. Because there are three Hall-effect sensors 50a, 50b, 50c, each of which can send two different signals, there are a total of eight different combinations of signals that can be sent to the controller. Each combination of signals is interpreted by the controller 16 as a set of instructions. More specifically, the controller 16 is programmed to interpret each combined signal as instructions for executing one of the programmed pump-operating programs. For example, a first combination of signals may be interpreted by the controller 16 as instructing the controller to execute a first pump-operating program, while a second combination of signals may be interpreted by the controller as instructing the controller to execute a second pump-operating program.

As can be understood, the operator interface 48 on the docking unit 14 allows an operator, such as medical personnel, to select a desired pump-operating program for the negative pressure unit 12. With the negative pressure unit 12 mounted on the docking unit 14, the operator selects the desired pump-operating program using the operator interface 48. The selection of pump-operating program instructs the controller 47 in the docking unit 14 to activate the actuator mechanism 44 to move each of the magnets 42a, 42b, 42c into one of the detection position and the non-detection position. With the magnets 42a, 42b, 42c moved into their respective selected positions, each Hall-effect sensors 50a, 50b, 50c either sense or do not sense the corresponding magnet, and send either the detection signal or the non-detection signal to the controller 16 in the negative pressure unit 12. The combination of signals of the three Hall-effect sensors 50a, 50b, 50c is received by the controller 16 as instructions for executing one of the programmed pump-operating programs.

With the desired pump-operating program selected, the negative pressure unit 12 can be removed from the docking unit 14. In the illustrated embodiment, the negative pressure unit 12 does not include an operator interface that allows an operator and/or patient change the selected pump-operating programs, although the negative pressure unit 12 can include a screen to allow the controller 16 to communicate data or status of therapy to the operator and/or patient. Accordingly, once the desired pump-operating program has been selected, it cannot be deselected or changed without remounting the negative pressure unit 12 on the docking unit 14 and selecting a new pump-operating program using the docking station. It is understood that the negative pressure unit 12 may include an operator interface (not shown) that allows the operator and/or the patient to activate and deactivate the negative pressure unit (i.e., turn the pump on and off) after it is removed from the docking unit 14. In such an embodiment, the controller 16 would execute the selected pump-operating program when the negative pressure unit 12 is activated.

Figure 4:
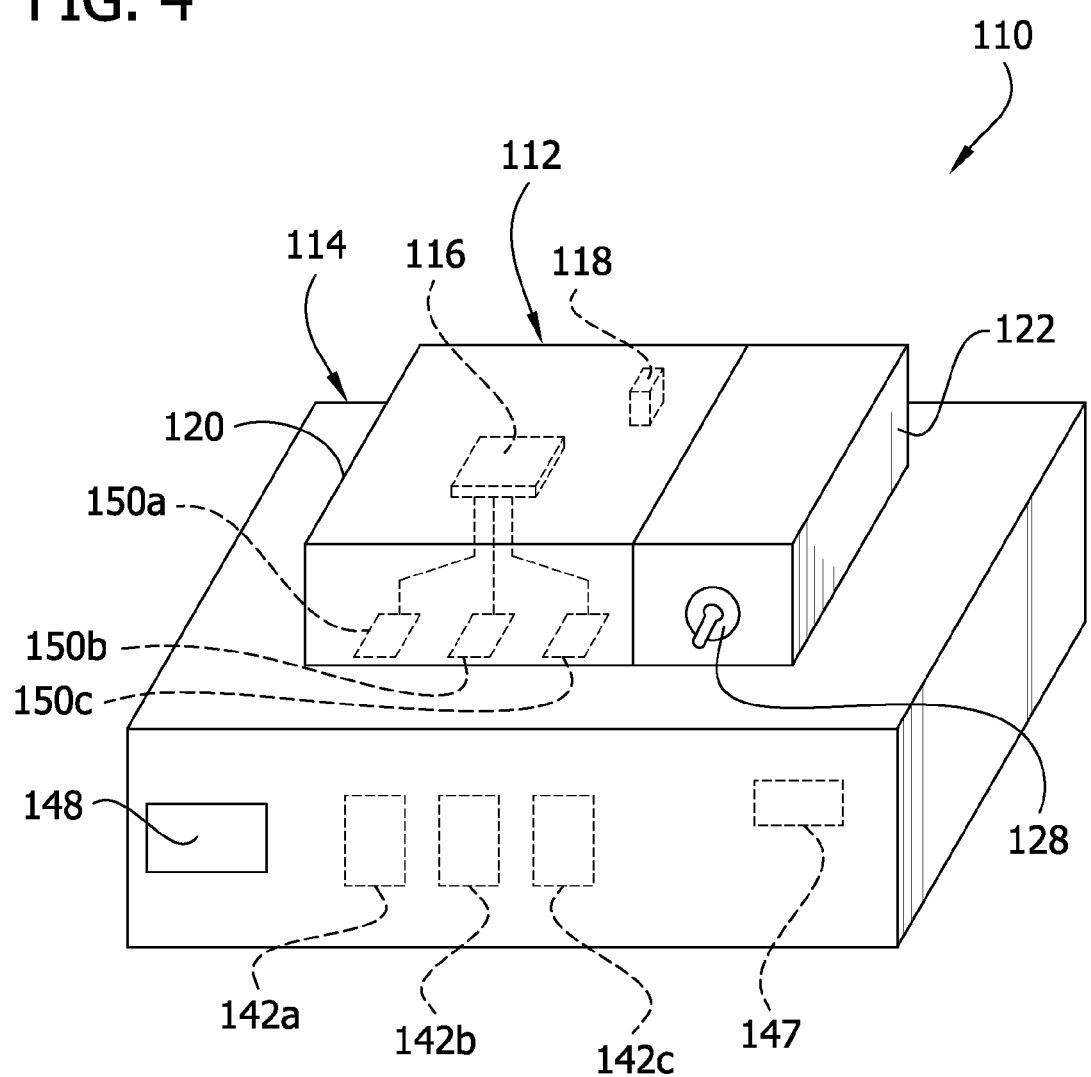
FIG. 4 is a schematic of a second embodiment of a negative pressure wound therapy system illustrating a negative pressure unit removed from a docking unit.

Referring to FIG. 4, in a second illustrated embodiment a docking unit 114 is similar to the docking unit 14 of the first embodiment and includes similar components indicated by corresponding reference numerals plus 100. Unlike the first docking unit 14, the second docking unit 114 includes electromagnetic sources 142a, 142b, 142c do not move with relative to the unit. In one example, the electromagnetic sources 142a, 142b, 142c are electromagnets, and the sensors 150a, 150b, 150c are Hall-effect sensors for detecting the magnetic field generated by the electromagnetic sources. Each electromagnet 142a, 142b, 142c generates a magnetic field (and electric field) when a current signal is applied to the electromagnet. Each of the magnetic fields is sensed by one of the Hall-effect sensors 150a, 150b, 150c when the signal current is applied. The controller 147 controls the activation or deactivation of each of the electromagnets 142a, 142b, 142c based on the pump-operating program selected at the operator interface 148. In one example, the current signal applied to each of the electromagnets 142a, 142b, 142c may be a pulsed current signal producing a corresponding pulsed magnetic field. The pulse magnetic field is detected by the Hall-effect sensors, and the controller 116 interprets the pulsed signal as instructions to execute a specific program.

Referring still to FIG. 4, in another example of the second illustrated embodiment, the electromagnetic sources 142a, 142b, 142c may comprise light sources and the sensors 150a, 150b, 150c may comprise light sensors for detecting the light generated by the light sources. Activation and deactivation of the individual light sources 142a, 142b, 142c are controlled by the controller 147 based on the pump-operating program selected at the operator interface 148. The docking unit 114 may include other types of electromagnetic sources and the negative pressure unit 112 may include corresponding electromagnetic sensors for detecting an output of the sources without departing from the scope of the present invention.

In a broad sense, the docking unit 14 includes one or more signal generators for generating one or more signals that are sensed by corresponding sensors in the negative pressure unit 12. In the first illustrated embodiment, the signal generators include the magnets 42a, 42b, 42c that generate magnetic fields. The docking unit 14 (e.g., through the actuator mechanism 44) is configured to control the individual positions of the magnets with respect to the sensor(s) 50a, 50b, 50c, when the negative pressure unit 12 is mounted on the docking unit. In the illustrated embodiment, magnetic flux densities of the magnets 42a, 42b, 42c sensed at the corresponding sensors 50a, 50b, 50c are controlled by moving the respective magnets closer to or farther from the corresponding sensors by independently rotating the disks 46a, 46b, 46c. In the second illustrated embodiment, the signal generators include the electromagnetic sources 142a, 142b, 142c, such as electromagnets that generate the magnetic fields as a function of the applied current signals, and the sensor include Hall-effect sensors. In another example, the electromagnetic sources 142a, 142b, 142c comprise light sources and the sensors include light sensors.

Figure 5:
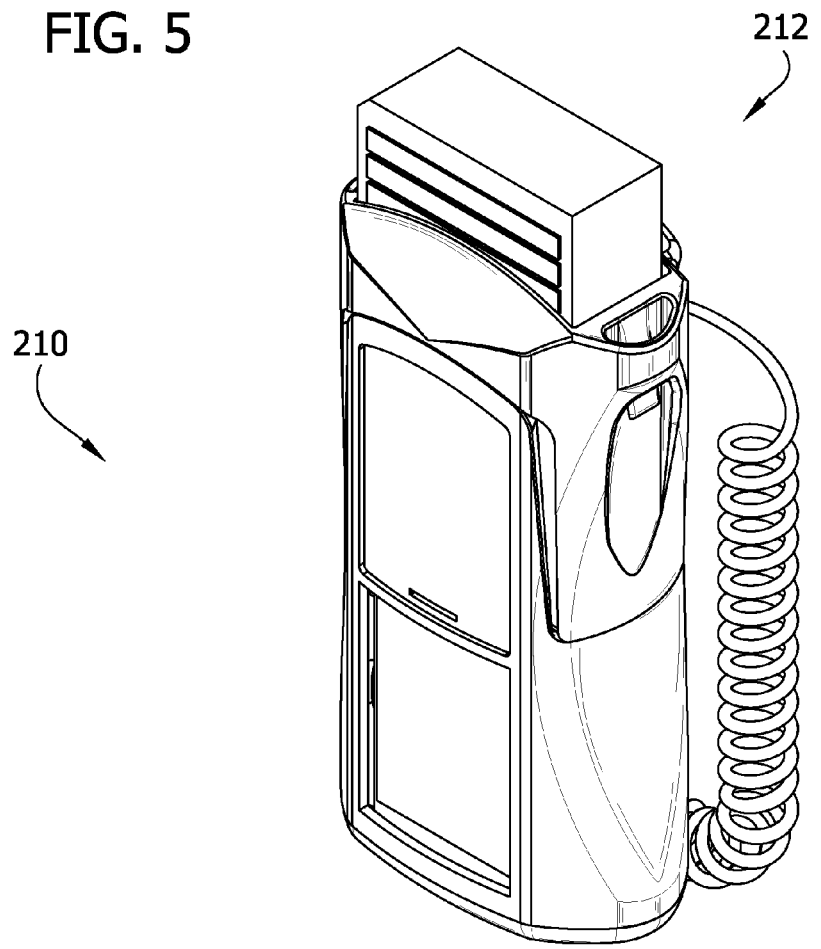
FIG. 5 is a schematic of a thermometer received in a docking unit.
Figure 5:
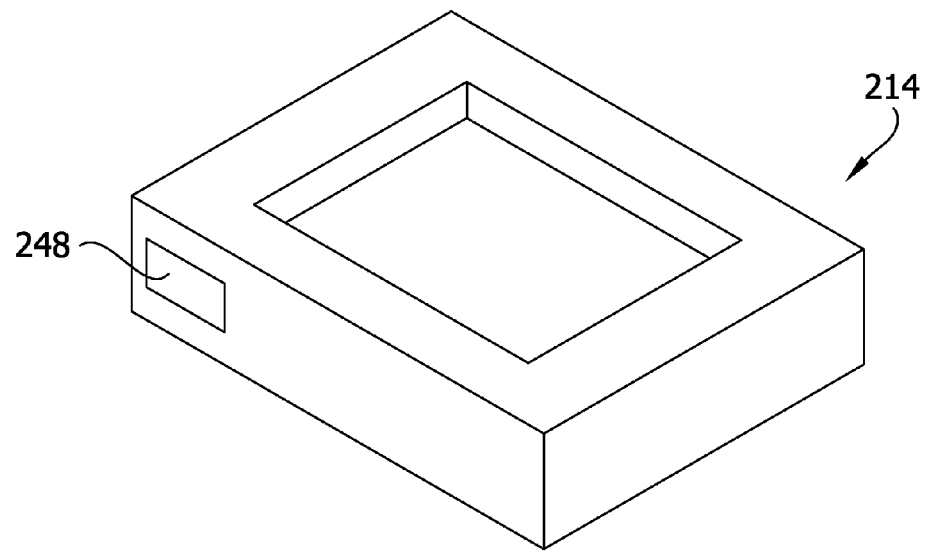

Referring to FIG. 5, another embodiment of a portable medical device system is an electrical thermometer system, generally indicated at 210. This embodiment is similar to the negative wound therapy system in that an electrical thermometer 212 is removably mountable on a docking unit 214. The docking unit communicates with a controller in the thermometer 212 to allow a user to select a program to be executed by the controller. The electronic thermometer 212 may or may not have a user interface to select or change the program. The docking unit 214 and the electronic thermometer 212 may include the same components as disclosed above with respect to either embodiment of the negative pressure wound therapy system 10, 110 that allow the docking unit to communicate with the thermometer. The docking unit 214 includes a user interface 248 and is configured to allow a user to instruct the controller in the thermometer to execute a program that changes or selects one or more of the following: beeper volume, prediction mode, anti-theft settings, display setting (backlight, contrast, ward name, language, etc.), settings lock, external communication settings, various diagnostic test (probe, LCD, battery, voltage, etc.), thermometer offset changes, and measurement scale (Fahrenheit vs Celsius).

Figure 6:
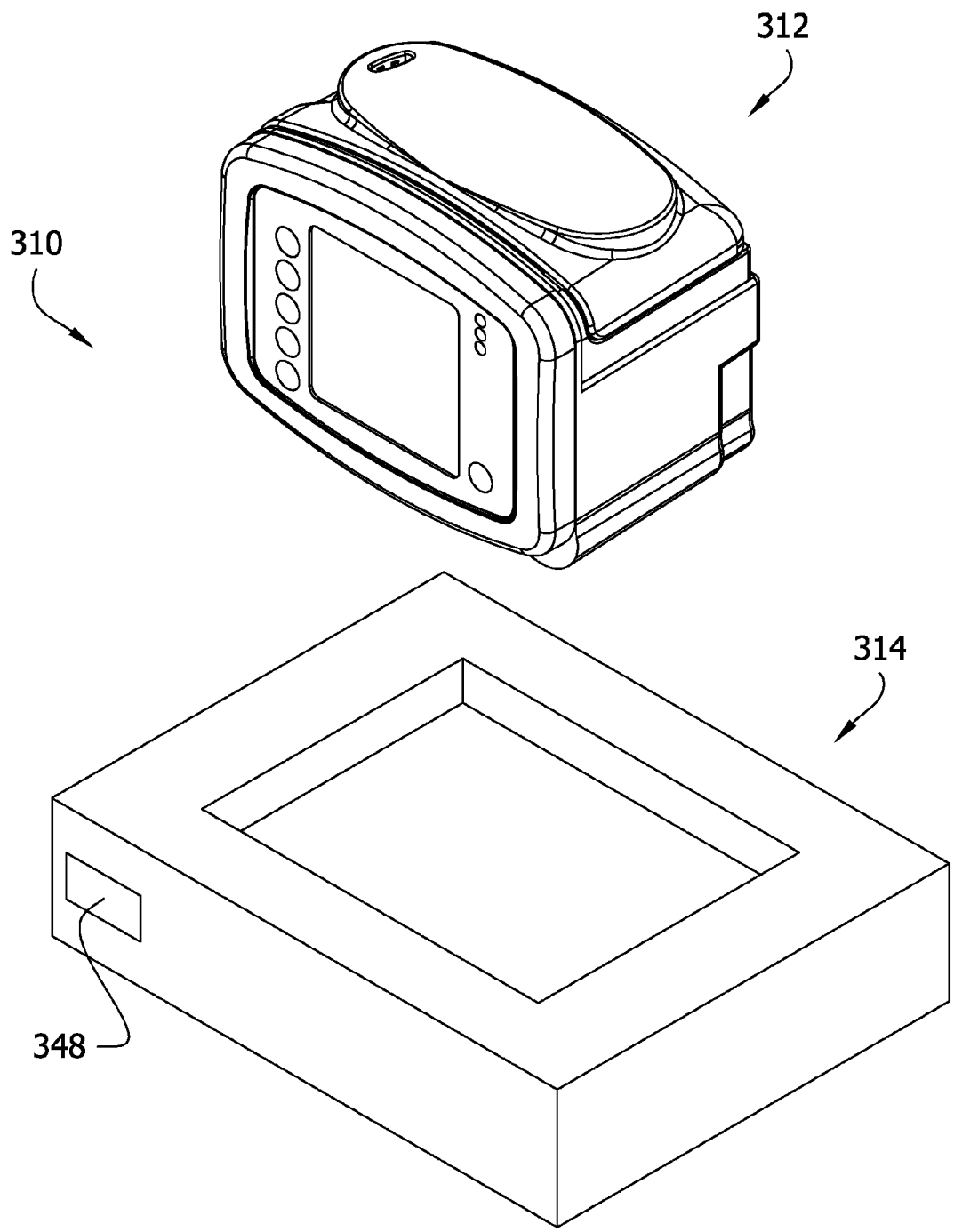
FIG. 6 is a schematic of a vascular compression control unit removed from a docking unit.

Referring to FIG. 6, another embodiment of a portable and programmable medical device system is an enteral feeding pump system, generally indicated at 310. This embodiment is similar to the negative pressure wound therapy system in that an enteral feeding pump 312 is removably mountable on a docking unit 314 whereby the docking unit communicates with a controller in the enteral feeding pump to allow a user to select and/or modify a program to be executed by the controller. The enteral feeding pump 312 may or may not have a user interface to select or change the program. The docking unit 314 and the enteral feeding pump 312 may include the same components as disclosed above with respect to either embodiment of the negative pressure wound therapy system 10, 110 that allow the docking unit to communicate with the enteral feeding pump. The docking unit 314 includes a user interface 348 and is configured to allow a user to instruct the controller in the enteral feeding pump 312 to execute a program that changes or selects one or more of the following: beeper volume, anti-theft settings, display setting (backlight, contrast, ward name, language, etc.), settings lock, external communication settings, various diagnostic test (probe, LCD, battery, voltage, etc.), bolus mode, continuous delivery mode, and pump-operating modes.

Figure 7:
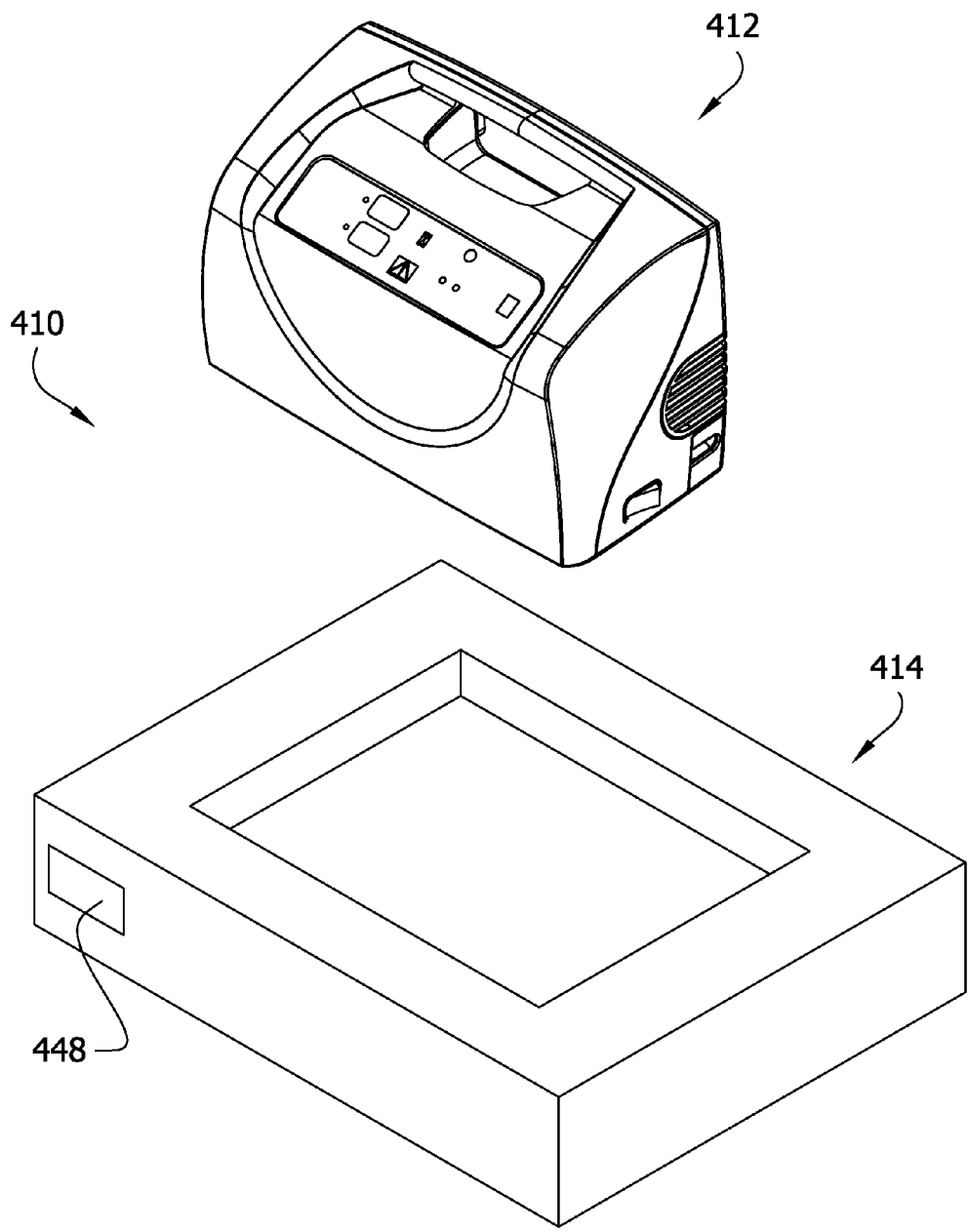
FIG. 7 is a schematic of an enteral feeding pump unit removed from a docking unit.

Referring to FIG. 7, another embodiment of a portable medical device system is a compression control unit system, generally indicated at 410, for supplying pressurized air to a compression device (e.g., compression sleeve for a leg or a compression foot cuff) for preventing deep vein thrombosis. This embodiment is similar to the negative pressure wound therapy system in that a compression control unit 412 is removably mountable on a docking unit 414 whereby the docking unit communicates with a controller in the compression control unit to allow a user to select a program to be executed by the controller. The compression control unit 412 may or may not have a user interface to select or change the program. The docking unit 414 and the compression control unit 412 may include the same components as disclosed above with respect to either embodiment of the negative pressure wound therapy system 10, 110 that allow the docking unit to communicate with the compression control unit. The docking unit 414 includes a user interface 448 and is configured to allow a user to instruct the controller to execute a program that changes or selects one or more of the following: beeper volume, anti-theft settings, display setting (backlight, contrast, ward name, language, etc.), settings lock, external communication settings, various diagnostic test (probe, LCD, battery, voltage, etc.), default pressure settings, and pump-operating modes.

Having described the invention in detail, it will be apparent that modifications and variations are possible without departing from the scope of the invention defined in the appended claims.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above constructions, products, and methods without departing from the scope of the invention, it is intended that all matter contained in the above description and shown in the accompanying drawings shall be interpreted as illustrative and not in a limiting sense.

What is claimed is:

1. A medical device system comprising:
a portable medical device including a controller programmed to selectively execute at least two programs for controlling at least one operation of the medical device; and
a docking unit on which the medical device can be removably mounted, the docking unit comprising an operator interface for selecting a program from said at least two programs, wherein the docking unit is configured to communicate with the controller of the medical device when the medical device is mounted on the docking unit to instruct the controller to execute the selected program, and wherein the controller of the medical device is configured to control the medical device according to the selected program when the medical device is removed from the docking unit;
the docking unit including at least one magnet disposed in the docking unit for generating a magnetic field, and the medical device including at least one magnet sensor for detecting the magnetic field, the magnet being movable in the docking unit to different positions to communicate the selection of different programs.

2. A medical device system as set forth in claim 1 wherein the magnet is movable between a detection position in which the magnet sensor detects the magnetic field, and a non-detection position in which the magnet sensor does not detect the magnetic field.

3. A medical device system as set forth in claim 2 wherein the at least one magnet sensor is a Hall-effect sensor.

4. A medical device system as set forth in claim 3 wherein the magnet is an electromagnet for generating a magnetic field as a function of an applied current signal.

5. A medical device system as set forth in claim 4 wherein the applied current signal is pulsed.

6. A medical device system as set forth in claim 2 wherein said docking unit comprises a plurality of magnets that are independently movable,
wherein said medical device comprises a plurality of magnet sensors, and
wherein the magnets and the magnet sensors are configured so that each magnet generates a magnetic field that is detectable by a single, dedicated one of the magnet sensors when the magnet is in the detection position.

7. A medical device system as set forth in claim 6 further comprising a plurality of independently rotatable disks, wherein each rotatable disk includes one of the magnets mounted thereon for independently moving the magnet.

8. A medical device system as set forth in claim 1 wherein the portable medical device is a negative pressure unit for use with negative pressure wound therapy, the negative pressure unit including a vacuum pump, and a canister in fluid communication with the vacuum pump for collecting exudates from a wound site, wherein the at least two programs are pump-operating programs for controlling operation of the pump, the negative pressure unit having no operator interface that allows the selected operating program to be deselected or changed.

9. A docking unit for a portable medical device including a magnet sensor and a controller programmed to selectively execute at least two programs for controlling operation of the medical device, the docking unit comprising:
an operator interface for selecting a program from said at least two programs; and
at least one magnet for generating a magnetic field, the magnet being movable in the docking unit to different positions in response to different selected programs for communicating the selected program to the medical device when the medical device is mounted on the docking unit.

10. A docking unit as set forth in claim 9 wherein the magnet is movable between a detection position in which the magnet sensor in the medical device detects the magnetic field, and a non-detection position in which the magnet sensor does not detect the magnetic field.

11. A docking unit as set forth in claim 10 wherein the magnet is an electromagnet for generating a magnetic field as a function of an applied current signal.

12. A docking unit as set forth in claim 9 further comprising a plurality of magnets mounted for individual movement in the docking unit.

13. A docking unit as set forth in claim 12 further comprising a disk for each magnet mounted for rotation in the docking unit, each disk mounting a respective one of the magnets.

* * * * *